United States Patent
Clendennen et al.

(10) Patent No.: US 9,284,583 B2
(45) Date of Patent: Mar. 15, 2016

(54) ENZYME-CATALYZED POLYOXYALKYLENE ESTERS

(71) Applicant: Eastman Chemical Company, Kingsport, TN (US)

(72) Inventors: Stephanie Kay Clendennen, Kingsport, TN (US); Jeffrey Michael Clauson, Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/333,154

(22) Filed: Jul. 16, 2014

(65) Prior Publication Data

US 2016/0017385 A1     Jan. 21, 2016

(51) Int. Cl.
    *C07C 69/34*      (2006.01)
    *C12P 7/62*      (2006.01)
    *C07C 69/22*      (2006.01)

(52) U.S. Cl.
    CPC ............. *C12P 7/625* (2013.01); *C07C 69/22* (2013.01); *C07C 69/34* (2013.01)

(58) Field of Classification Search
    CPC .......... C07C 69/34; C07C 69/22; C12P 7/625
    See application file for complete search history.

(56) References Cited

U.S. PATENT DOCUMENTS

| | | | |
|---|---|---|---|
| 2,151,185 A | 3/1939 | Carruthers et al. | |
| 2,158,107 A | 5/1939 | Carruthers et al. | |
| 2,573,701 A | 11/1951 | Filachione et al. | |
| 7,491,836 B2 * | 2/2009 | von Corswant et al. | 554/213 |
| 2005/0255536 A1 * | 11/2005 | Okada et al. | 435/19 |
| 2012/0040395 A1 | 2/2012 | Clendennen | |
| 2013/0177951 A1 | 7/2013 | Burk et al. | |

OTHER PUBLICATIONS

Jenssen et al, Biotechnology Letters, 1994, 16(2), 163-168.*
HERA Human & Environmental Risk Assessment on ingredients of European household cleaning products, Alcohol Ethoxylates, Version 2.0, Sep. 2009. http://www.heraproject.com/files/34-f-09%20hera%20ae%20report%20version%202%20-%203%20sept%2009.pdf.
ATSDR, 2012, Public Health Statement for 1,4-Dioxane, accessed Nov. 21, 2013: http://www.atsdr.cdc.gov/toxprofiles/tp187-c1.pdf.
CTFA, 2007, "CTFA Statement on Dioxane" accessed Nov. 21, 2013 at: http://www.personalcarecouncil.org/newsroom/20070201.
FDA, 2007, "1,4-dioxane—A Manufacturing Byproduct" Accessed Nov. 21, 2013 at http://www.fda.gov/cosmetics/productandingredientsafety/potentialcontaminants/ucm101566.htm.
Agency for Toxic Substances & Disease Registry Toxic Substances Portal, ATSDR Toxicological Profile for 1,4 Dioxane (www.atsdr.cdc.gov/ToxProfiles/).
Gu, Qu-Ming et al., "Enzyme-Catalyzed Condensation Reactions for 5 Polymer Modifications", American Chemical Society, (2005) p. 433.
Notification of Transmittal of the International Search Report and the Written Opinion of the International Searching Authority; date of mailing Oct. 6, 2015; for International Application No. PCT/US15/40255.
Cosmetic Ingredient Review Expert Panel, et al.; "Final Report on the Safety Assessment of PEG-25 Propylene Glycol Stearate, PEG-75 Propylene Glycol Stearate, PEG-120 Propylene Glycol Stearate, PEG-10 Propylene Glycol, PEG-8 Propylene Glycol Cocoate, and PEG-55 Propylene Glycol Oleate"; International Journal of Toxicology; 2001; vol. 20 (Suppl. 4); pp. 13-26.

* cited by examiner

*Primary Examiner* — Shailendra Kumar
(74) *Attorney, Agent, or Firm* — Dennis V. Carmen; Matthew W. Smith

(57) ABSTRACT

One aspect of the present invention is a polyoxyalkylene ester composition comprising the reaction product of a polyoxyalkylated alcohol or polyol reactant and an acyl donor wherein the ester has greater than about 85 weight percent of a fully acylated polyoxyalkylene ester, less than about 15 percent of a partially acylated polyoxyalkylene ester, less than about 5 parts per million 1,4-dioxane and an acid number of less than about 20. Another aspect of the invention is a process for making the polyoxyalkylene ester composition that includes the steps of contacting a reaction mixture of an polyoxyalkylated alcohol or polyol reactant and an acyl donor reactant in a reactor and in the presence of an enzymatic catalyst under esterification conditions and recovering the polyoxyalkylene ester.

20 Claims, No Drawings

US 9,284,583 B2

ENZYME-CATALYZED POLYOXYALKYLENE ESTERS

1. FIELD OF THE INVENTION

The present invention relates to a polyoxyalkylene ester composition and more particularly to the esterification of an ethoxylated intermediate reactant alcohol with an acyl donor wherein the polyoxyalkylene ester product has less than about 15 weight % of a partially acylated polyoxyalkylene ester and a low amount of 1,4-dioxane byproduct. In another aspect, the present invention relates to a method for esterifying an ethoxylated intermediate reactant alcohol with an acyl donor comprising wherein the polyoxyalkylene ester product has less than about 15 weight % of a partially acylated polyoxyalkylene ester and a low amount of 1,4-dioxane byproduct, the method includes contacting the reactants with an enzyme catalyst under esterification conditions and recovering the polyoxyalkylene ester product.

2. BACKGROUND

Polyethylene glycol or PEG of the formula $H(OCH_2CH_2)$n-OH with n equal to 4 to 900 corresponding to average molar masses of from 180 to 40000 g/mol, are generally prepared by polymerizing ethylene oxide with water or polyhydric alcohols. Ethoxylate esters and particularly esters of PEGs are employed in a large number of areas and applications because of their interesting properties. A large number of these applications involve the polyethylene glycol ester making superficial contact with the skin of living creatures, especially humans, or being administered orally or parenterally to humans or animals. Examples of such applications are solvents for active ingredients, flavorings or fragrances in medicinal drops, solutions for injection, dietary supplements, tablets, ointments, sticks, suppositories or gelatin capsules; plasticizers for coatings of film-coated tablets; binders in tablets; humectants in toothpastes; moisturizers and/or conditioners in shower preparations, shampoos, cream rinses, hair treatments, soaps, liquid soaps, hair sprays, hair gels, after-shave products, face packs, sunscreen products, creams or lotions; ingredient of multiphase products such as two-phase shower preparations, two-phase foam baths or three-phase bath oils; and active ingredient in eye drops, laxatives or solutions having antiapoptotic activity.

Alcohol ethoxylates and PEGs by themselves are not genotoxic, mutagenic, carcinogenic or sensitizers and are readily biodegraded. When ethoxylate esters are made with a traditional chemical process, exposure of an ethoxylated intermediate to heat and acidic conditions can lead to the formation of the carcinogenic byproduct 1,4-dioxane. Trace levels of 1,4-dioxane have raised concerns about the use of ethoxylated surfactants in formulated home, laundry and personal care products.

The amount of 1,4-dioxane that is allowed to be produced by a production plant can be limited by specified concessions. In these cases, a limit on the amount of 1,4-dioxane thus leads indirectly to a limit on the production capacity of a ester polyol production plant. The 1,4-dioxane formed as a by-product also has the effect of reducing the yield of the desired product, since, as described, part of the diethylene glycol used is removed from the reaction mixture in the form of 1,4-dioxane instead of being incorporated into the ester produced.

Accordingly, there is a need for fully acylated polyoxyalkylene ester composition having less than about 20 ppm of 1,4-dioxane and having a high molar yield of the fully acylated ester constituent. There is also a need for a process of making a fully acylated polyoxyalkylene ester composition.

3. SUMMARY OF THE INVENTION

Briefly, one aspect of the present invention is a polyoxyalkylene ester having greater than about 85 weight percent of a fully acylated polyoxyalkylene ester, less than about 15 weight percent of a partially acylated polyoxyalkylene ester, less than about 20 parts per million (ppm) 1,4-dioxane and an acid number of less than about 30.

Another aspect of the present invention is a process for making the above fully acylated polyoxyalkylene ester that includes the steps of contacting a reaction mixture of a polyoxyalkylated alcohol or polyol reactant and an acyl donor reactant in the presence of an enzyme catalyst under esterification conditions, wherein said enzyme catalyst has a concentration of greater than about 0.1 weight % to less than 100 weight %, based on the total weight of the reactants; and recovering the fully acylated polyoxyalkylene ester.

These and other objects and advantages of the present invention will become more apparent to those skilled in the art in view of the following description and the accompanying drawings. It is to be understood that the inventive concept is not to be considered limited to the constructions disclosed herein but instead by the scope of the appended claims.

DETAILED DESCRIPTION OF THE INVENTION

In accordance with one aspect of the present invention, a fully acylated polyoxyalkylene ester composition is disclosed that is the reaction product of a polyoxyalkylated alcohol or polyol reactant and an acyl donor, wherein the ester has greater than about 85 weight percent of the fully acylated polyoxyalkylene ester, less than about 15 weight percent of a partially acylated polyoxyalkylene ester, less than about 5 parts per million 1,4-dioxane and an acid number of less than about 30.

The polyoxyalkylene esters used in the invention contain at least one ester group and at least one ether group. In preparing the polyoxyalkylene ester of the present invention, the process includes the steps of: in a reaction zone, contacting a reaction mixture of an polyoxyalkylated alcohol or polyol reactant and an acyl donor reactant in the presence of an enzyme catalyst under esterification conditions, wherein said enzyme catalyst has a concentration of greater than about 0.1 weight % to less than 100 weight %, based on the total weight of the reactants; and recovering the fully acylated polyoxyalkylene ester.

The polyoxylalkylene alcohol or polyol reactant has at least one ether group, and has an average hydroxyl functionality of at least 0.8, or at least 0.9, or at least 1 in the case of a polyoxylalkylene alcohol (typically made with a mono-hydric initiator), or an average functionality of about 1.8 to 8, or 1.8 to 6, or 1.8 to 3 in the case of a polyoxyalkylene polyol.

Any polyoxyalkylated alcohol or polyol can be used. Polyoxylalkylene alcohols and polyols can be made by reacting an alkylene oxide, such as ethylene oxide or propylene oxide or butylene oxide, preferably at least ethylene oxide, with an initiator compound having at least one active hydrogen in the presence of a catalyst, such as a base compound.

Any suitable catalyst can be used to make the polyoxyalkylene alcohol or polyol. polyoxyalkylene alcohols or polyols can be produced by anionic polymerization with alkali hydroxides such as sodium hydroxide or potassium hydroxide or alkali alcoholates, such as sodium methylate, sodium ethylate, or potassium ethylate or potassium isopropylate as catalysts and with the addition of at least one initiator molecule having a reactive hydrogen, or by cationic polymerization with Lewis acids such as antimony pentachloride, boron trifluoride etherate, etc., or bleaching earth as catalysts from one or more alkylene oxides with 2 to 4 carbons in the alkylene radical.

The initiator molecule has at least one active hydrogen atom, desirably with a molecular weight less than 500, or less than 400, or less than 300, or less than 250, or less than 200. Examples of monohydric initiator compounds having hydroxyl groups include methanol, ethanol, 2-ethylhexanol, and other oxo-alcohols; and poly-hydric initiators having hydroxyl groups include ethylene glycol, 1,2-propylene glycol, 1,3-propylene glycol, 1,4-butanediol, 1,5-pentanediol, 1,6-hexanediol, 1,10-decanediol, diethylene glycol, dipropylene glycol, trimethylolpropanes, tripropylene glycol, tetraethylene glycol, tetrapropylene glycol, tetramethylene glycol, 1,4-cyclohexane-dimethanol, lactones, e.g., ε-caprolactone or hydroxycarboxylic acids, e.g., w-hydroxycaproic acid, hydroquinone, resorcinol, bisphenols, and monoesters of glycerine; glycerine, trimethylolethane, N-alkylphenylenediamines, mono-, dio, and trialkanolamines, pentaerythritol, sorbitol, sorbitan, monosaccharides and disaccharides containing 5 or 6 carbon atoms per saccharide unit such as ribose, arabinose, cyclose, xylose, and lyxose allose, altrose, glucose, mannose, glucose, idose, galactose, talose, fructose, and sorbose, maltose, cellobiose, sucrose, and lactose, and mixtures of any of the above. More desired polyols of the class of saccharides are glucose, fructose, and sucrose. Suitable amine initiator materials include aliphatic and cycloaliphatic amines and mixtures thereof, having at least one primary amino group. Specific non-limiting examples of aliphatic amines include monoamines having 1 to 12, or 1 to 6 carbon atoms, such as methylamine, ethylamine, butylamine, hexylamine, octylamine, decylamine and dodecylamine; aliphatic diamines such as 1,2-diaminoethane, propylene diamine, 1,4-diaminobutane, 1,6-diaminohexane, 2,2-dimethyl-,3-propanediamine, 2-methyl-1,5-pentadiamine, 2,5-dimethyl-2,5-hexanediamine, and 4-aminomethyloctane-1,8-diamine, and amino acid-based polyamines such as lysine methyl ester, lysine aminoethyl ester and cystine dimethyl ester; cycloaliphatic monoamines of 5 to 12, preferably of 5 to 8, carbon atoms in the cycloalkyl radical, such as cyclohexylamine and cyclo-octylamine and preferably cycloaliphatic diamines of 6 to 13 carbon atoms, such as cyclohexylenediamine, 4,4'-, 4,2'-, and 2,2'-diaminocyclohexylmethane and mixtures thereof; aromatic monoamines of 6 to 18 carbon atoms, such as aniline, benzylamine, toluidine and naphthylamine and aromatic diamines of 6 to 15 carbon atoms, such as phenylenediamine, naphthylenediamine, fluorenediamine, diphenyldiamine, anthracenediamine, and preferably 2,4- and 2,6-toluenediamine and 4,4'-, 2,4'-, and 2,2'-diaminodiphenylmethane, and aromatic polyamines such as 2,4,6-triaminotoluene, mixtures of polyphenyl-polymethylene-polyamines, and mixtures of diaminidiphenylmethanes and polyphenyl-polymethylene-polyamines. Typical amine initiators include ethylenediamine, propylenediamine, decanediamine, 4,4'-diaminophenylmethane, 4,4'-diaminocyclohexylmethane, and toluenediamine.

Suitable initiator molecules also include alkanolamines such as ethanolamine, diethanolamine, N-methyl- and N-ethylethanolamine, N-methyl- and N-ethyldiethanolamine and triethanolamine plus ammonia.

If desired, the initiator molecules can be fatty alcohols having 8-24 carbon atoms. The fatty alcohol initiator molecule can be branched or unbranched, primary or secondary alcohol, and can be saturated or unsaturated or polyunsaturated. If a branched fatty alcohol is used, it can have alkyl branching of a length of 3 or less carbon atoms. Examples of fatty alcohol initiator molecules include octyl alcohol, nonyl alcohol, decyl alcohol, dodecyl alcohol, tetradecyl alcohol, cetyl alcohol, lauryl alcohol, palmityl alcohol, stearyl alcohol, hydrogenated tallow alcohol, and mixtures thereof.

Addition of alkylene oxide to the initiator molecules may take place simultaneously or sequentially when more than one alkylene oxide is used, resulting in block, heteric, and block-heteric polyoxyalkylene polyethers. Preferable is a poly-ether oxyalkylated with at least ethylene oxide, or at least 70 mole % ethylene oxide, or at least 80 mole % ethylene oxide, or at least 90 mole % ethylene oxide, or at least 95 mole % ethylene oxide, based on all the moles of alkylene oxide reacted into the polyoxyalkylene alcohol or polyol.

The polyoxyalkene alcohol or polyol can have from 1 to about 500 oxyalkylene units added to each active hydrogen on the initiator molecule. The final poloxylalkylene alcohol or polyol can have from 3 to about 300, or 3 to about 200, or 3 to about 150 alkylene oxide units, such as ethylene oxide units.

If desired, the polyoxyalkylene alcohol or polyol can contain from 1 to about 20 $C_2$-$C_3$ alkylene oxide units and mixtures thereof. Desirable alkylene oxide units are ethylene glycol, propylene glycol, 1,3-propylene glycol. Mixed ethylene oxide/propylene oxide polyoxyalkylene alcohols and polyols may be copolymers of polyoxypropylene and polyoxyethylene having terminal oxyethylene groups.

A broad range of ethoxylated alcohol or polyol intermediates can be purchased, such as those used in polyurethane production and polyethylene glycol. PEG methyl ether or PEG ethyl ether is another common starting material, with a single terminal hydroxyl group.

The molecular weight (Mn) of the polyoxyalkylene alcohols and polyols are not particularly limited and can range from 150 and up to 10,000.

To make the polyoxyalkylene esters, an acyl donor is reacted with the polyoxylalkylene alcohol or polyol. To increase yield, the target stoichiometric ratio of acyl donors to hydroxyl groups on the polyoxyalkylene alcohol or polyol is about at least 1:1. However, the stoichiometry of the starting materials may be varied to afford different product mixtures, as is known to those skilled in the art, resulting in hydroxyl groups of the polyoxyalkylene alcohols and polyols being partially and/or fully acylated. A fully acylated polyoxylkylene alcohol or polyol molecule is one in which all hydroxyl groups on the polyoxyalkylene alcohol or polyol molecule are acylated. A partially acylated polyoxylkylene alcohol or polyol molecule is one in which not all hydroxyl groups on the polyoxyalkylene alcohol or polyol molecule are acylated, including a polyoxylkylene alcohol or polyol molecule in which none of the hydroxyl groups are acylated.

Desirably, the composition of the invention contains 85 weight percent or more, or at least 87 weight percent or more, or at least 89 weight percent or more, or at least 90 weight percent or more, or at least 92 weight percent or more, or at least 94 weight percent or more, or at least 95 weight percent or more, or at least 96 weight percent or more, or at least 97 weight percent or more, or at least 98 weight percent or more, or at least 99 weight percent or more, or at least 99.5 weight percent or more, or at least 99.8 weight percent or more of a fully acylated polyoxyalkylene ester.

Desirably, the composition of the invention also contains a partially acylated polyoxyalkylene ester in an amount of zero and if present in an amount of up to 15 weight percent or less, or up to 13 weight percent or less, or up to 11 weight percent or less, or up to 10 weight percent or less, or up to 9 weight percent or less, or up to 7 weight percent or less, or up to 5 weight percent or less, or up to 4 weight percent or less, or up to 3 weight percent or less, or up to 2 weight percent or less, or up to 1 weight percent or less. As noted above, the partially acylated polyoxyalkylene alcohol or polyol can include those molecules in which none of the hydroxyl groups are acylated, such as reactant molecules in the composition that are left unreacted.

The composition may contain and 5 parts per million or less of 1,4-dioxane, or 4 ppm or less of 1,4-dioxane, or 3 ppm or less of 1,4-dioxane, or 2 ppm or less of 1,4-dioxane, or 1 ppm or less of 1,4-dioxane.

The composition can have an acid number of 30 or less, or 25 or less, or 22 or less, or 20 or less, or 19 or less, or 17 or less, or 16 or less, or 15 or less, or 13 or less, or 11 or less, or 10 or less, or 9 or less, of mg of KOH per gram of sample.

In each of the above cases, the amounts are based on the weight of the composition.

Desirably, the acyl donor is a carboxylic acid having 3 or more carbons in length, such as a fatty acid, and can also be a mixture of acids. Useful acyl donors include carboxylic acids such as mono-, di-, and polycarboxylic acids or anhydrides thereof. The carboxylic acid can be linear, branched, unbranched, saturated, or unsaturated and can include linear, branched, and cyclic $C_3$-$C_{40}$ aliphatic carboxylic acids and $C_8$-$C_{40}$ aromatic carboxylic acids. The acyl donor may also be the methyl or ethyl ester of these carboxylic acids or carboxylic acid mixtures. One skilled in the art will recognize the term $C_3$-$C_{40}$ includes carboxylic acids having from 3 to 40 carbon atoms, inclusive and includes carboxylic acids having from 4 to 40, 5 to 40, 6 to 40, 7 to 40, 8 to 40, 9 to 40, 10 to 40, 11 to 40, 12 to 40, 13 to 40, 14 to 40, 15 to 40, 16 to 40, 17 to 40, 18 to 40, 19 to 40, 20 to 40, 21 to 40, 22 to 40, 23 to 40, 24 to 40, 25 to 40, 26 to 40, 27 to 40, 28 to 40, 29 to 40, 30 to 40, 31 to 40, 32 to 40, 33 to 40, 34 to 40, 35 to 40, 36 to 40, 37 to 40, 38 to 40, 39 to 40, 5 to 40, 6 to 40, 7 to 40, 8 to 40, 9 to 40, 10 to 40, 11 to 40, 12 to 40, 13 to 40, 14 to 40, 15 to 40, 16 to 40, 17 to 40, 18 to 40, 19 to 40, 20 to 40, 21 to 40, 22 to 40, 23 to 40, 24 to 40, 25 to 40, 26 to 40, 27 to 40, 28 to 40, 29 to 40, 30 to 40, 31 to 40, 32 to 40, 33 to 40, 34 to 40, 35 to 40, 36 to 40, 37 to 40, 38 to 40, 39 to 40, 4 to 39, 5 to 39, 6 to 39, 7 to 39, 8 to 39, 9 to 39, 10 to 39, 11 to 39, 12 to 39, 13 to 39, 14 to 39, 15 to 39, 16 to 39, 17 to 39, 18 to 39, 19 to 39, 20 to 39, 21 to 39, 22 to 39, 23 to 39, 24 to 39, 25 to 39, 26 to 39, 27 to 39, 28 to 39, 29 to 39, 30 to 39, 31 to 39, 32 to 39, 33 to 39, 34 to 39, 35 to 39, 36 to 39, 37 to 39, 38 to 39, 4 to 38, 5 to 38, 6 to 38, 7 to 38, 8 to 38, 9 to 38, 10 to 38, 11 to 38, 12 to 38, 13 to 38, 14 to 38, 15 to 38, 16 to 38, 17 to 38, 18 to 38, 19 to 38, 20 to 38, 21 to 38, 22 to 38, 23 to 38, 24 to 38, 25 to 38, 26 to 38, 27 to 38, 28 to 38, 29 to 38, 30 to 38, 31 to 38, 32 to 38, 33 to 38, 34 to 38, 35 to 38, 36 to 38, 37 to 38, 4 to 37, 5 to 37, 6 to 37, 7 to 37, 8 to 37, 9 to 37, 10 to 37, 11 to 37, 12 to 37, 13 to 37, 14 to 37, 15 to 37, 16 to 37, 17 to 37, 18 to 37, 19 to 37, 20 to 37, 21 to 37, 22 to 37, 23 to 37, 24 to 37, 25 to 37, 26 to 37, 27 to 37, 28 to 37, 29 to 37, 30 to 37, 31 to 37, 32 to 37, 33 to 37, 34 to 37, 35 to 37, 36 to 37, 4 to 36, 5 to 36, 6 to 36, 7 to 36, 8 to 36, 9 to 36, 10 to 36, 11 to 36, 12 to 36, 13 to 36, 14 to 36, 15 to 36, 16 to 36, 17 to 36, 18 to 36, 19 to 36, 20 to 36, 21 to 36, 22 to 36, 23 to 36, 24 to 36, 25 to 36, 26 to 36, 27 to 36, 28 to 36, 29 to 36, 30 to 36, 31 to 36, 32 to 36, 33 to 36, 34 to 36, 35 to 36, 4 to 35, 5 to 35, 6 to 35, 7 to 35, 8 to 35, 9 to 35, 10 to 35, 11 to 35, 12 to 35, 13 to 35, 14 to 35, 15 to 35, 16 to 35, 17 to 35, 18 to 35, 19 to 35, 20 to 35, 21 to 35, 22 to 35, 23 to 35, 24 to 35, 25 to 35, 26 to 35, 27 to 35, 28 to 35, 29 to 35, 30 to 35, 31 to 35, 32 to 35, 33 to 35, 34 to 35, 4 to 34, 5 to 34, 6 to 34, 7 to 34, 8 to 34, 9 to 34, 10 to 34, 11 to 34, 12 to 34, 13 to 34, 14 to 34, 15 to 34, 16 to 34, 17 to 34, 18 to 34, 19 to 34, 20 to 34, 21 to 34, 22 to 34, 23 to 34, 24 to 34, 25 to 34, 26 to 34, 27 to 34, 28 to 34, 29 to 34, 30 to 34, 31 to 34, 32 to 34, 33 to 34, 4 to 33, 5 to 33, 6 to 33, 7 to 33, 8 to 33, 9 to 33, 10 to 33, 11 to 33, 12 to 33, 13 to 33, 14 to 33, 15 to 33, 16 to 33, 17 to 33, 18 to 33, 19 to 33, 20 to 33, 21 to 33, 22 to 33, 23 to 33, 24 to 33, 25 to 33, 26 to 33, 27 to 33, 28 to 33, 29 to 33, 30 to 33, 31 to 33, 32 to 33, 4 to 32, 5 to 32, 6 to 32, 7 to 32, 8 to 32, 9 to 32, 10 to 32, 11 to 32, 12 to 32, 13 to 32, 14 to 32, 15 to 32, 16 to 32, 17 to 32, 18 to 32, 19 to 32, 20 to 32, 21 to 32, 22 to 32, 23 to 32, 24 to 32, 25 to 32, 26 to 32, 27 to 32, 28 to 32, 29 to 32, 30 to 32, 31 to 32, 4 to 31, 5 to 31, 6 to 31, 7 to 31, 8 to 31, 9 to 31, 10 to 31, 11 to 31, 12 to 31, 13 to 31, 14 to 31, 15 to 31, 16 to 31, 17 to 31, 18 to 31, 19 to 31, 20 to 31, 21 to 31, 22 to 31, 23 to 31, 24 to 31, 25 to 31, 26 to 31, 27 to 31, 28 to 31, 29 to 31, 30 to 31, 4 to 30, 5 to 30, 6 to 30, 7 to 30, 8 to 30, 9 to 30, 10 to 30, 11 to 30, 12 to 30, 13 to 30, 14 to 30, 15 to 30, 16 to 30, 17 to 30, 18 to 30, 19 to 30, 20 to 30, 21 to 30, 22 to 30, 23 to 30, 24 to 30, 25 to 30, 26 to 30, 27 to 30, 28 to 30, 29 to 30, 4 to 29, 5 to 29, 6 to 29, 7 to 29, 8 to 29, 9 to 29, 10 to 29, 11 to 29, 12 to 29, 13 to 29, 14 to 29, 15 to 29, 16 to 29, 17 to 29, 18 to 29, 19 to 29, 20 to 29, 21 to 29, 22 to 29, 23 to 29, 24 to 29, 25 to 29, 26 to 29, 27 to 29, 28 to 29, 4 to 28, 5 to 28, 6 to 28, 7 to 28, 8 to 28, 9 to 28, 10 to 28, 11 to 28, 12 to 28, 13 to 28, 14 to 28, 15 to 28, 16 to 28, 17 to 28, 18 to 28, 19 to 28, 20 to 28, 21 to 28, 22 to 28, 23 to 28, 24 to 28, 25 to 28, 26 to 28, 27 to 28, 4 to 27, 5 to 27, 6 to 27, 7 to 27, 8 to 27, 9 to 27, 10 to 27, 11 to 27, 12 to 27, 13 to 27, 14 to 27, 15 to 27, 16 to 27, 17 to 27, 18 to 27, 19 to 27, 20 to 27, 21 to 27, 22 to 27, 23 to 27, 24 to 27, 25 to 27, 26 to 27, 4 to 26, 5 to 26, 6 to 26, 7 to 26, 8 to 26, 9 to 26, 10 to 26, 11 to 26, 12 to 26, 13 to 26, 14 to 26, 15 to 26, 16 to 26, 17 to 26, 18 to 26, 19 to 26, 20 to 26, 21 to 26, 22 to 26, 23 to 26, 24 to 26, 25 to 26, 4 to 25, 5 to 25, 6 to 25, 7 to 25, 8 to 25, 9 to 25, 10 to 25, 11 to 25, 12 to 25, 13 to 25, 14 to 25, 15 to 25, 16 to 25, 17 to 25, 18 to 25, 19 to 25, 20 to 25, 21 to 25, 22 to 25, 23 to 25, 24 to 25, 4 to 24, 5 to 24, 6 to 24, 7 to 24, 8 to 24, 9 to 24, 10 to 24, 11 to 24, 12 to 24, 13 to 24, 14 to 24, 15 to 24, 16 to 24, 17 to 24, 18 to 24, 19 to 24, 20 to 24, 21 to 24, 22 to 24, 23 to 24, 4 to 23, 5 to 23, 6 to 23, 7 to 23, 8 to 23, 9 to 23, 10 to 23, 11 to 23, 12 to 23, 13 to 23, 14 to 23, 15 to 23, 16 to 23, 17 to 23, 18 to 23, 19 to 23, 20 to 23, 21 to 23, 22 to 23, 4 to 22, 5 to 22, 6 to 22, 7 to 22, 8 to 22, 9 to 22, 10 to 22, 11 to 22, 12 to 22, 13 to 22, 14 to 22, 15 to 22, 16 to 22, 17 to 22, 18 to 22, 19 to 22, 20 to 22, 21 to 22, 4 to 21, 5 to 21, 6 to 21, 7 to 21, 8 to 21, 9 to 21, 10 to 21, 11 to 21, 12 to 21, 13 to 21, 14 to 21, 15 to 21, 16 to 21, 17 to 21, 18 to 21, 19 to 21, 20 to 21, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, 19 to 20, 4 to 19, 5 to 19, 6 to 19, 7 to 19, 8 to 19, 9 to 19, 10 to 19, 11 to 19, 12 to 19, 13 to 19, 14 to 19, 15 to 19, 16 to 19, 17 to 19, 18 to 19, 4 to 18, 5 to 18, 6 to 18, 7 to 18, 8 to 18, 9 to 18, 10 to 18, 11 to 18, 12 to 18, 13 to 18, 14 to 18, 15 to 18, 16 to 18, 17 to 18, 4 to 17, 5 to 17, 6 to 17, 7 to 17, 8 to 17, 9 to 17, 10 to 17, 11 to 17, 12 to 17, 13 to 17, 14 to 17, 15 to 17, 16 to 17, 4 to 16, 5 to 16, 6 to 16, 7 to 16, 8 to 16, 9 to 16, 10 to 16, 11 to 16, 12 to 16, 13 to 16, 14 to 16, 15 to 16, 4 to 15, 5 to 15, 6 to 15, 7 to 15, 8 to 15, 9 to 15, 10 to 15, 11 to 15, 12 to 15, 13 to 15, 14 to 15, 4 to 14, 5 to 14, 6 to 14, 7 to 14, 8 to 14, 9 to 14, 10 to 14, 11 to 14, 12 to 14, 13 to 14, 4 to 13, 5 to 13, 6 to 13, 7 to 13, 8 to 13, 9 to 13, 10 to 13, 11 to 13, 12 to 13, 4 to 12, 5 to 12, 6 to 12, 7 to 12, 8 to 12, 9 to 12, 10 to 12, 11 to 12, 4 to 11, 5 to 11, 6 to 11, 7 to 11, 8 to 11, 9 to 11, 10 to 11, 4 to 10, 5 to 10, 6 to 10, 7 to 10, 8 to 10, 9 to 10, 4 to 9, 5 to 9, 6 to 9, 7 to 9, 8 to 9, 4 to 8, 5 to 8, 6 to 8, 7 to 8, 4 to 7, 5 to 7, 6 to 7, 4 to 6, and 5 to 6 carbon atoms.

Suitable carboxylic acids for use in the invention include, for example, acetic acid, propionic acid, decanoic acid, benzoic acid, stearic acid, isostearic acid, lauric acid, linoleic acid, oleic acid, adipic acid, suberic acid, malonic acid, succinic acid, glutaric acid, pimelic acid, itaconic acid, octanoic acid, palmitic acid, suberic acid, azelaic acid, sebacic acid, maleic acid, fumaric acid, citraconic acid, phthalic acid, isophthalic acid, terephthalic acid, dimer acids, tetrahydrophthalic acid, halogenated phthalic and tetrahydrophthalic acids, 2-ethylhexanoic acid, myristic acid, erucic acid, behenic acid, arachidic acid, lignoceric acid, cerotic acid, pamitoleic acid, myristoleic acid, arachidonic acid, butyric acid, isobutyric acid, valeric acid, hexanoic acid, heptanoic acid, and methyl and ethyl esters of these acids.

If an anhydride is used, the carboxylic acid is generated in situ by combining the anhydride and at least about one molar equivalent of water. For example, maleic anhydride, water, catalyst, and the polyoxyalkylene alcohol or polyol can be combined and heated at a relatively mild temperature that is effective to cause hydrolysis of the anhydride to produce maleic acid. Specific examples of suitable anhydrides that can be used include, but are not limited to, acetic anhydride, propionic anhydride, maleic anhydride, phthalic anhydride, succinic anhydride, lauric anhydride, octanoic anhydride, palmitic anhydride, tetrahydrophthalic anhydride, citraconic anhydride, itaconic anhydride, and aryl-, alkyl- and halogen-substituted derivatives of these. Mixtures of anhydrides may also be used.

The amount of polyoxyalkylene alcohols and polyols used in making the polyoxyalkylene ester is preferably at least about one equivalent of carboxylic acid end group for each free hydroxyl group. For example, in the case where the polyoxylalkylene molecule is a diol, the target molar ratio of acyl to diol is at least from about 1.95:1, or at least 2:1.

In the present invention, an immobilized heat-stable enzyme is used for reacting the polyoxyalkylated alcohol or polyol reactant and an acyl donor starting materials described above. Suitable thermostable enzymes include, but are not limited to: hydrolase, esterase, lipase, acylase and protease. Moreover, within each class of enzyme it is known that there are various types or sources of each enzyme. For example, it is known lipase may be obtained from *Pseudomonas fluorescens*, *Pseudomonas capecia*, *Porcine pancreatic* lipase, *Candida antarctica* lipase B, and *Mucor miehei* lipase; galactosidase can be obtained from *Escherichia coli* and *Aspergillus oryzae* to name a few. Preferred enzymes are lipases. These lipases may be in the form of whole cells, isolated native enzymes, or immobilized on supports. Non-limiting examples of these lipases include but are not limited to Lipase PS (from *Pseudomonas* sp), Lipase PS-C (from *Psuedomonas* sp immobilized on ceramic), Lipase PS-D (from *Pseudomonas* sp immobilized on diatomaceous earth), Lipoprime 50T, Lipozyme TL IM, or Novozym 435 (from *Candida antarctica* immobilized on acrylic resin). One or more enzyme catalysts can be immobilized on a porous support.

The enzyme catalyst is immobilized on a carrier substrate. Suitable materials include organic and inorganic materials such as, for example, carbon such as activated carbon, graphene oxide and carbon nanotubes; inorganic materials such as glass, glass wool, silica gel, metal oxides, clay, diatomaceous earth, iron oxide, and magnetic beads; natural polymeric materials and modified natural polymers such as calcium alginate, glyoxyl agarose, chitosan, gelatin, cellulose, cellulose esters, carboxymethylcellulose, silk, wool, cotton fibers, and coconut fibers; synthetic polymeric materials such as polyethylene, polypropylene, poly(ethylene glycol), polystyrene, polyacrylamide, poly(acrylonitrile), poly(phenylendediamine), poly(ethyleneimine), polyvinyl alcohol, polyvinyl chloride, poly(ether sulfone), phenol-formalin resin, acrylic resin, fluoropolymers, anionic exchange resin, cationic exchange resin, epoxy-activated supports, amino-activated supports, octadecyl-activated supports, including copolymers, blends, composites and combinations of any of the above.

The carrier substrate is selected from a synthetic polymeric material having porosity as the physical form, for example, porous polyethylene, porous polypropylene, porous phenol formalin resin, porous fluoropolymer, porous acrylic resin and porous polystyrene, including copolymers, composites and blends, are more preferred. In the present invention, various immobilizing carriers other than above may also be used so long as they do not hinder the development of the enzymatic reactivity. The porous support material may be in the form of a membrane, film, tape, fiber, hollow fiber, tube, braid, sponge, foam, particle, or other 3-dimensional forms. As a method of immobilizing the thermostable enzyme as described above, any of the methods known in the art of carrier bonding, crosslinking and inclusion may be used. For example, if desired, the enzyme catalyst may be immobilized via non-covalently binding the catalyst to a porous support.

The immobilized catalyst desirably maintains enzyme binding and activity even after multiple re-uses. For example, the immobilized catalyst maintains catalytic activity for between 2 and 50 reuses, between 3 and 30 reuses or even between 5 and 10 reuses. Maintaining catalytic activity is intended to mean that the immobilized catalyst maintains at least 70% of initial catalytic activity after at least 10 uses, at least 80% of initial catalytic activity after at least 10 reuses, or even at least 90% of initial catalytic activity after at least 10 reuses.

A flat sheet membrane, sponge, braid, fiber, hollow fiber, particle or 3-dimensional form can be loaded with catalyst, then assembled into a reactor system. A pre-assembled reactor system, such as a flow-through or zero to 100% by-pass cartridge, containing the porous support, can be loaded in situ with enzyme catalyst, such as by immersion in the enzyme solution or flow of the enzyme solution through or across the support.

The amount of catalytic enzyme immobilized on the carrier substrate, can be from 0.001 to about 1000 mg to one gram of the immobilizing carrier; or 0.01 to 750 mg to one gram of the immobilizing carrier; or 0.01 to about 500 mg to one gram of the immobilizing carrier; or 0.01 to 300 mg to one gram of the immobilizing carrier.

The amount of the heat stable immobilized enzymatic catalyst in the reaction zone has no particular restrictions, although the amount can preferably be from 0.1 to 10,000 parts by weight, or from about 1 to about 5,000 parts by weight, or from about 10 to 5,000 parts by weight, or from about 50 to about 3,000 parts by weight, wherein all parts are based on 100 parts by weight of the fatty acid or its ester.

Alternatively, the amount of the thermostable immobilized enzymatic catalyst in the reaction zone ranges from about 0.1 to about 100 weight %, inclusive. The amount of the thermostable immobilized enzymatic catalyst in the reaction zone ranges from about 0.1 weight % to 80 weight %, or 0.1 weight % to 70 weight %, or 0.1 weight % to 60 weight %, or 0.1 weight % to 50 weight %, or 0.1 weight % to 40 weight %, or 0.1 weight % to 30 weight %, or 0.1 weight % to 20 weight %, or 0.1 weight % to 15 weight %, or 1.0 to about 10 weight %, inclusive, or from about 2 weight % to about 10 weight %, inclusive, or from about 3 weight % to about 8 weight %, inclusive, or 1.0 weight % to 10 weight %, wherein the above weight percentages are based on the total weight of the reactants.

One skilled in the art will understand that, as noted before, the ranges delineated include all ranges therebetween and are inclusive of the end points. For example, the range of 0.1 to 15 weight % includes not only the whole numbers between 0.1 to 15, but also all fractional portions or parts therebetween, which are too numerous to express herein but are clearly within the understanding of anyone having even minor math acumen and are be understood to be expressly included in the description of the present invention.

In addition to the quantity of enzyme incorporated on the supporting substrate one skilled in the art will understand that the quality or viability (rate of reaction) of the enzyme is equally important. Although it is believed that various kinds of immobilized thermostable enzymes may be used singularly or in mixtures the chosen enzyme(s) should have sufficient heat resistance so that after possessing the enzyme should have a minimum specific activity greater than about 10% of a pure enzyme, desirably greater than 40%, more desirably greater than 50% and, even more desirably, greater than 75%, and most desirably greater than 90% of the enzyme retains activity after immobilizing. For instance, thermostable lipase derived from *Candida antarctica* and lipase derived from *Mucor miehei* (both available from Novozymes), are thermostable and suitable since they have excellent heat resistance.

Enzyme activity equals moles of substrate converted per unit time which also equals rate times reaction volume, i.e., enzyme activity=moles of substrate converted per unit time=rate×reaction volume. Enzyme activity is a measure of the quantity of active enzyme present and is dependent on conditions. The SI unit is the katal. One katal equals one mole per second (1 mol/sec), and generally refers to that of the assumed natural target substrate of the enzyme. A more practical and commonly used value is an enzyme unit (U) which equals 1 micromole/min which equals 16.67 nanokatals. One U is defined as the amount of enzyme that produces a certain amount of enzymatic activity, i.e., the conversion of 1 micromole of substrate per minute at a temperature of 25° C. and a pH of about 7.

Enzyme activity can also be given as that of certain standardized substrates, such as gelatin, then measured in gelatin digesting units (GDU), or milk proteins, then measured in milk clotting units (MCU). The units GDU and MCU are based on how fast one gram of the enzyme will digest gelatin or milk proteins, respectively. 1 GDU equals approximately 1.5 MCU.

The specific activity of an enzyme is another common unit. Specific activity is a measure of enzyme processivity, at a specific (usually saturating) substrate concentration, and is usually constant for a pure enzyme. This is the activity of an enzyme per milligram of total protein (expressed in μmol/min·mg). Specific activity gives a measurement of enzyme purity in the mixture. It is the amount of product formed by an enzyme in a given amount of time under given conditions per milligram of total proteins. Specific activity is equal to the rate of reaction multiplied by the volume of reaction divided by the mass of total protein (SA=(rxn rate×rxn vol)/mass of total protein).

For elimination of errors arising from differences in cultivation batches and/or misfolded enzyme etc. an active site titration needs to be done. This is a measure of the amount of active enzyme, calculated by titrating the amount of active sites present by employing an irreversible inhibitor. If the molecular weight of the enzyme is known, the turnover number, (expressed as μmol product/sec·umol-1 of active enzyme), can be calculated from the specific activity. The turnover number can be visualized as the number of times each enzyme molecule carries out its catalytic cycle per second. The percent purity is 100%×(specific activity of enzyme sample/specific activity of pure enzyme). The impure sample has lower specific activity because some of the mass is not actually enzyme. If the specific activity of 100% pure enzyme is known, then an impure sample will have a lower specific activity, allowing purity to be calculated.

One skilled in the art will understand that the reaction conditions for making the fully acylated polyoxyalkylene ester using a thermostable immobilized lipase can be adjusted to suit the reactants, carrier catalyst loading, catalyst specific activity as well as the catalyst type and specie. The esterification reaction temperature of the reactants can be from about 20° C. to about 120° C., or from about 30° C. to about 100° C., or from about 40° C. to about 80° C. The time for completing the reaction can be from about 0.5 hours to about 72 hours, and desirably from about 0.5 to about 48 hours and more desirably from about 1 to about 36 hours.

One skilled in the art will understand that, all ranges delineated explicitly herein include all ranges implicitly therebetween. For example, the range for catalyst activity, catalyst loadings, reaction temperatures and times includes not only the whole numbers of the respective expressed ranges, but also all fractional portions or parts therebetween, which are too numerous to express herein but are clearly within the knowledge and understanding of anyone having a rudimentary understanding of math and such ranges are be understood to be expressly included in this description.

Further, producing the polyoxyalkylene ester by the process according to the present invention, it can be conducted by adopting, for example, a method of passing liquid reactants into a column packed with the immobilized enzymatic catalyst (packed column system), or using a batch or semi-batch method of introducing the liquid reactants and an immobilized enzyme into a reaction vessel and then conducting reaction by stirring and/or shaking until the desire level of reaction has been achieved, or by the method of continuously conducting the reaction in a vessel, pipe or tube.

Further, in the present invention, organic solvents may be mixed together within such a range as not hindering the reaction of the present invention. In this case, there can be mentioned, as other organic solvents, for example, aromatic hydrocarbons such as benzene, toluene, xylene and phenol, ketones such as acetone, aliphatic hydrocarbons such as n-hexane and iso-octane, cycloaliphatic hydrocarbons such as cyclopentane and cyclohexane, ethers such as dimethyl ether, diethyl ether and dioxane, and halogenated hydrocarbons such as carbon tetrachloride and chloroform.

In the process according to the present invention, water or a lower alcohol having from 1 to 4 carbon atoms is by-product of the enzymatic reaction to make the ester. Desirably, removing such by-products drives the equilibrium toward the formation of desired products and increases yield and reaction efficiency. Generally, it is preferred to remove the by-products such that the concentration of the by-products in the system is less than about 1 weight % for efficiently proceeding the reaction. Various processes are known for removing the water of reaction formed in the ester formation from the polyol and the carboxylic acids. For example, the water of reaction formed can be distilled out of the reaction vessel together with the excess carboxylic acid and passed into a downstream phase separator in which carboxylic acid and water separate according to solubility properties. Another method of removing the by-products includes, for example, removing by adsorption using zeolite, molecular sieve or desiccant. In some cases, the carboxylic acid used also forms an azeotrope with water under the reaction conditions and is capable of removing the water of reaction as an entraining agent. Other means include azeotropic distillation may be used in the presence of an added water-immiscible solvent; introducing dry air or inert gas into a reaction vessel and removing the by-products by evaporation into gases; or a method of reducing the pressure in the reaction vessel and evaporizing the by-products out of the reaction vessel. By properly combining the removing method with the enzymatic reaction device as described above, synthesis reaction can be conducted at high efficiency.

Removing any reaction by-products can be facilitated by inducing a vacuum on the reaction zone or introducing an inert gas, preferably nitrogen, into the reaction zone, sufficient to remove the by-products to the desired concentration, desirably less than about 10 weight %, and more desirably less than about 1 weight % of the reactants, and most desirably less than about 0.5 weight % of the reactants.

After the completion of the reaction, the fully acylated polyoxyalkylene ester in the reaction products can be recovered by separating the product from the immobilized catalyst and collected using any customary method, such as filtration, vacuum filtration, rotary filtration, and centrifuging.

In accordance with another aspect of the present invention is a fully acylated polyoxyalkylene ester composition prepared by reacting a polyoxyalkylated alcohol or polyol reactant and an acyl donor in the presence of an enzymatic catalyst to produce a ester having greater than about 85 weight percent of the fully acylated polyoxyalkylene ester, less than about 15 weight percent of a partially acylated polyoxyalkylene ester, less than about 5 parts per million 1,4-dioxane and having an acid number of less than about 20.

The polyoxyalkylene ester composition desirably has about 90 weight percent or more, or 95 weight percent or more, of the fully acylated polyoxyalkylene ester; 9 weight percent, or less or 3 weight percent or less, of a partially acylated polyoxyalkylene ester; 2 parts per million, or less or 1 part per million or less, of 1,4-dioxane and has an acid number of about 20 or less or 18 or less.

For example, the polyoxyalkylene ester composition prepared in accordance with the invention can have greater than about 95 weight percent of the fully acylated polyoxyalkylene ester, less than about 3 weight percent of a partially acylated polyoxyalkylene ester, less than about 1 parts per million 1,4-dioxane and an acid number of less than about 18.

The polyoxyalkylene ester that is the reaction product of a polyoxyalkylated alcohol or polyol reactant and an acyl donor of the process of the present invention described above can be any desired polyoxyalkylene ester, such as PEG-10 Laurate, PEG-10 methylether caprate, PEG-10 methylether caprylate, PEG-10 methylether caprylate/caprate, PEG-10 methylether cocoate, PEG-10 methylether isostearate, PEG-10 methylether laurate, PEG-10 methylether myristate, PEG-10 methylether oleate, PEG-10 methylether palmitate, PEG-10 methylether stearate, PEG-10 Propylene Glycol esters, PEG-10 Sorbitan Laurate, PEG-10 Stearate, PEG-10 Sunflower Glycerides, PEG-100 methylether caprate, PEG-100 methylether caprylate, PEG-100 methylether caprylate/caprate, PEG-100 methylether cocoate, PEG-100 methylether isostearate, PEG-100 methylether laurate, PEG-100 methylether myristate, PEG-100 methylether oleate, PEG-100 methylether palmitate, PEG-100 methylether stearate, PEG-100 Stearate, PEG-12 Dilaurate, PEG-12 Distearate, PEG-12 Glyceryl Dimyristate, PEG-12 Glyceryl Distearate, PEG-12 Laurate, PEG-12 Stearate, PEG-12 methylether caprate, PEG-12 methylether caprylate, PEG-12 methylether caprylate/caprate, PEG-12 methylether cocoate, PEG-12 methylether isostearate, PEG-12 methylether laurate, PEG-12 methylether myristate, PEG-12 methylether oleate, PEG-12 methylether palmitate, PEG-12 methylether stearate, PEG-120 Distearate, PEG-120 Methyl Glucose Dioleate, PEG-120 Methyl Glucose Trioleate, PEG-120 Propylene Glycol Stearate, PEG-14 Laurate, PEG-150 Dilaurate, PEG-150 Distearate, PEG-150 Laurate, PEG-150 Pentaerythrityl Tetrastearate, PEG-16 Macadamia Glycerides, PEG-16 methylether caprate, PEG-16 methylether caprylate, PEG-16 methylether caprylate/caprate, PEG-16 methylether cocoate, PEG-16 methylether isostearate, PEG-16 methylether laurate, PEG-16 methylether myristate, PEG-16 methylether oleate, PEG-16 methylether palmitate, PEG-16 methylether stearate, PEG-160 Sorbitan Triisostearate, PEG-175 Distearate, PEG-18 Glyceryl Oleate, PEG-18 Glyceryl Oleate Cocoate, PEG-18 Sorbitan Trioleate, PEG-2 Dilaurate, PEG-2 Distearate, PEG-2 Laurate, PEG-2 Sorbitan Isostearate, PEG-2 Stearate, PEG-20 Almond Glycerides, PEG-20 Dilaurate, PEG-20 Distearate, PEG-20 Glycerides, PEG-20 Laurate, PEG-20 methylether caprate, PEG-20 methylether caprylate, PEG-20 methylether caprylate/caprate, PEG-20 methylether cocoate, PEG-20 methylether isostearate, PEG-20 methylether laurate, PEG-20 methylether myristate, PEG-20 methylether oleate, PEG-20 methylether palmitate, PEG-20 methylether stearate, PEG-20 Oleate, PEG-20 Sorbitan Cocoate, PEG-20 Sorbitan Isostearate, PEG-20 Sorbitan Tetraoleate, PEG-20 Sorbitan Triisostearate, PEG-20 Stearate, PEG-200 Glyceryl Stearate, PEG-200 Hydrogenated Glycerides, PEG-200 Hydrogenated Glyceryl Palmate, PEG-200 Laurate, PEG-21 Stearate, PEG-23 Laurate, PEG-25 Hydrogenated Castor Oil, PEG-25 Propylene Glycol Stearate, PEG-3 Caprate, PEG-3 Caprylate, PEG-3 Caprylate/Caprate, PEG-3 Di(Caprylate/Caprate), PEG-3 Dicaprate, PEG-3 Dicaprylate, PEG-3 Dilaurate, PEG-3 Distearate, PEG-3 Ester of C5-C9 Acids, PEG-3 Laurate, PEG-3 Sorbitan Oleate, PEG-3 Sorbitan Stearate, PEG-30 Dipolyhydroxystearate, PEG-30 Glyceryl Cocoate, PEG-30 Glyceryl Stearate, PEG-30 Sorbitan Tetraoleate, PEG-30 Sorbitol Tetraoleate Laurate, PEG-30 Stearate, PEG-32 Dilaurate, PEG-32 Distearate, PEG-32 Laurate, PEG-32 Stearate, PEG-35 Castor Oil, PEG-4 Caprate, PEG-4 Caprylate, PEG-4 Caprylate/Caprate, PEG-4 Di(Caprylate/Caprate), PEG-4 Dicaprate, PEG-4 Dicaprylate, PEG-4 Dierucate, PEG-4 Diheptanoate, PEG-4 Dilaurate, PEG-4 Dioleate, PEG-4 Distearate, PEG-4 Laurate, PEG-4 Olivate, PEG-40 Castor Oil, PEG-40 Distearate, PEG-40 Glyceryl Cocoate, PEG-40 Hydrogenated Castor Oil, PEG-40 methylether caprate, PEG-40 methylether caprylate, PEG-40 methylether caprylate/caprate, PEG-40 methylether cocoate, PEG-40 methylether isostearate, PEG-40 methylether laurate, PEG-40 methylether myristate, PEG-40 methylether oleate, PEG-40 methylether palmitate, PEG-40 methylether stearate, PEG-40 Sorbitan Diisostearate, PEG-40 Sorbitan Hexaoleate, PEG-40 Sorbitan Laurate, PEG-40 Sorbitan Perisostearate, PEG-40 Sorbitan Peroleate, PEG-40 Sorbitan Stearate, PEG-40 Sorbitan Tetraoleate, PEG-40 Stearate, PEG-44 Sorbitan Laurate, PEG-45 Palm Kernel Glycerides, PEG-5 Ethylhexanoate, PEG-5 Glyceryl Stearate, PEG-5 Sorbitan Isostearate, PEG-50 Distearate, PEG-50 Hydrogenated Palmamide, PEG-50 Sorbitan Hexaoleate, PEG-50 Stearate, PEG-55 Propylene Glycol Oleate, PEG-6 Caprate, PEG-6 Caprylate, PEG-6 Caprylate/Caprate, PEG-6 Caprylic/Capric Glycerides, PEG-6 Cocamide, PEG-6 Di(Caprylate/Caprate), PEG-6 Dicaprate, PEG-6 Dicaprylate, PEG-6 Dilaurate, PEG-6 Distearate, PEG-6 Isostearate, PEG-6 Laurate, PEG-6 methylether caprate, PEG-6 methylether caprylate, PEG-6 methylether caprylate/caprate, PEG-6 methylether cocoate, PEG-6 methylether isostearate, PEG-6 methylether laurate, PEG-6 methylether myristate, PEG-6 methylether oleate, PEG-6 methylether palmitate, PEG-6 methylether stearate, PEG-6 Sorbitan Oleate, PEG-6 Sorbitan Stearate, PEG-6 Stearate, PEG-60 Almond Glycerides, PEG-60 Glyceryl Isostearate, PEG-60 Hydrogenated Castor Oil, PEG-60 methylether caprate, PEG-60 methylether caprylate, PEG-60 methylether caprylate/caprate, PEG-60 methylether cocoate, PEG-60 methylether isostearate, PEG-60 methylether laurate, PEG-60 methylether myristate, PEG-60 methylether oleate, PEG-60 methylether palmitate, PEG-60 methylether stearate, PEG-60 Sorbitan Stearate, PEG-60 Sorbitan Tetraoleate, PEG-60 Sorbitan Tetrastearate, PEG-60 Sorbitol Tetrastearate, PEG-7 Caprylic/Capric, Glycerides, PEG-7 Glyceryl Cocoate, PEG-7 Hydrogenated Castor Oil, PEG-7 Olivate, PEG-70 Mango Glycerides, PEG-75 Dilaurate, PEG-75 Distearate, PEG-75 Laurate, PEG-75 Propylene Glycol Stearate, PEG-75 Shea Butter Glycerides, PEG-75 Sorbitan Laurate, PEG-75 Stearate, PEG-78 Glyceryl Cocoate, PEG-8 Dicocoate, PEG-8 Dilaurate, PEG-8 Dioleate, PEG-8 Distearate, PEG-8 Isostearate, PEG-8 Laurate, PEG-8 Oleate, PEG-8 Olive Oil Ester, PEG-8 Propylene Glycol Cocoate, PEG-8 Ricinoleate, PEG-8 Stearate, PEG-80 Glyceryl Cocoate, PEG-80 Sorbitan Laurate, PEG-80 Sorbitan Palmitate, PEG-9 Distearate, PEG-9 Laurate, PEG-90 Glyceryl Isostearate, Polysorbate-20, Polysorbate-60, and Polysorbate-80.

The present invention is illustrated in greater detail by the specific examples presented below. It is to be understood that these examples are illustrative embodiments and are not intended to be limiting of the invention, but rather are to be construed broadly within the scope and content of the appended claims. All parts and percentages in the examples are on a weight basis unless otherwise stated.

COMPARATIVE EXAMPLE 1

Enzymatic Preparation of PEG-4 Dilaurate (PEG 200 Dilaurate)

A lauric acid diester of poly (ethylene glycol) having an average molecular weight of 200 (average of 4 EO units) was prepared in accordance with the method as described in Gu, Qu-Ming et al., "Enzyme-Catalyzed Condensation Reactions for Polymer Modifications", American Chemical Society, (2005) page 433. Lauric acid (16.16 g; 81 mmol; 1.9 equivalents) available from Sigma Aldrich was combined with poly (ethylene glycol) (PEG-4) from Sigma Aldrich with an average molecular weight of 204 (8.49 g; 42.5 mmol; 1.0 equiv) in a 100-mL 3 neck round bottom flask equipped with a magnetic stir bar. Immobilized lipase Novozym®435 available from Novozymes was added to the flask at an amount of 1 g/kg reactants, (0.1 weight % based on the combined weight of the PEG and lauric acid). The mixture was stirred with a magnetic stir bar and heated with a heating mantle to 60° C. and kept under a vacuum of between 10 and 20 mm Hg.

Progress of the esterification reactions was monitored using high performance liquid chromatography (HPLC). At regular intervals approximately 10 microliters of reaction mixture was withdrawn and solubilized in 1 milliliter of methanol. An Agilent 1100 high performance liquid chromatograph equipped with a Zorbax SB-C8 4.6×150 mm 3.5 micron HPLC column and a SofTA model 1400 evaporative light scattering detector were utilized for sample analysis.

HPLC method details: A solvent gradient from 97% water/ 0.1% trifluoroacetic acid (TFA) 3% tetrahydrofuran to 3% H2O/0.1% TFA 97% tetrahydrofuran was applied over 25 minutes. From 25 to 27 min the gradient was shifted back to start conditions: 97% H2O/0.1% TFA 3% tetrahydrofuran, then held at those conditions for 2 minutes. Total run time was 29 minutes with no post run period. The method used a 2 microliter sample injection, 30° C. column temperature, 1 milliliter/min flow rate, and all solvents were of HPLC grade.

After 20 hours under these conditions the final reaction mixture was separated from the catalyst by vacuum filtration. The product was bottled and analyzed by HPLC to determine conversion of PEG-4 to PEG-4 dilaurate along with acid number determination to assess residual levels of unreacted fatty acid. The resulting product analysis indicated 53.2% diester, 31.3% monoester, 14.3% free lauric acid and 1.2% PEG-4, based on combined area percent of reactants and products. The acid number (mg KOH/g) was 88.5. The results are tabulated in Table 3 below.

EXAMPLE 2

A lauric acid diester of poly(ethylene glycol) having an average molecular weight of 200 was prepared in accordance with the method of the present invention. Lauric acid (17.00 g; 2.0 equivalents) available from Sigma Aldrich was combined with poly (ethylene glycol) (PEG-4) from Sigma Aldrich with an average molecular weight of 204 (8.48 g; 1.0 equiv) in a 100-mL 3 neck round bottom flask equipped with a magnetic stir bar. Immobilized lipase Novozym®435 was added to the flask at an amount of 1.26 grams (50 g/kg reactants; 5 weight % based on the combined weight of the PEG and lauric acid). The flask was submerged into a temperature controlled oil bath and mounted above a magnetic stirrer. A thermocouple was mounted in the oil bath and connected to a temperature controller. The bath temperature was set to 55° C. and stirring was started. A septum stopper was inserted into the neck 1 of 3. The septum was pierced with 18 gauge×6 inch stainless needle which was used to sparge nitrogen into the reaction mixture at a rate of 250 ml/min. Into neck 2 of 3 a stopper was inserted for reaction sampling access. A hose adapter was inserted into neck 3 of 3 and was routed to a manifold for escaping sparge gas and maintaining the inert atmosphere inside flask. Sampling of the reaction was begun when the reaction mixture reached homogeneity.

Progress of the esterification reaction was monitored via high performance liquid chromatography (HPLC) as described in Comparative Example 1 above.

After 24 hours the reaction was stopped and filtered warm through Whatman® qualitative filter paper, Grade 2 under vacuum. The filtered product was transferred to an amber bottle and sampled for final purity. The resulting product analysis indicated 99.1% PEG-4 dilaurate and 0.9% PEG-4 monolaurate, based on combined area percent of reactants and the product. The acid number (mg KOH/g) was 8.2. The results are tabulated in Table 3 below.

EXAMPLE 3

Enzymatic Preparation of PEG-150 Distearate

A stearic acid diester of polyethylene glycol having a molecular weight of 6000 (average of 150 ethylene oxide units) was prepared in accordance with the present invention. Stearic acid (23.73 g) available from SAFC was combined with polyethylene glycol PEG MW 6000 (249.95 g) available from Aldrich in a 3 neck 2 liter round bottom flask equipped with a magnetic stir bar. Immobilized lipase Novozym®435 was added to the flask at an amount of 8.16 grams, (3 wt % of total starting materials). The flask was submerged into a temperature controlled oil bath and mounted above a magnetic stirrer.

The flask was placed into a temperature controlled heating mantle and mounted above a magnetic stirrer. A thermocouple was inserted into neck 1 of 3 and connected to a temperature controller. The bath temperature was set to 65° C. and stirring was started. A medium porosity gas dispersion tube was inserted into neck 2 of 3 to sparge nitrogen into the reaction mixture at a rate of 250 ml/min. A hose adapter was attached to neck 3 of 3 and routed to a manifold for escaping sparge gas and maintaining the inert atmosphere inside flask. Sampling of the reaction was begun when the reaction mixture reached homogeneity. After 20 hours an additional 2.37 g of stearic acid (10 wt % of original charge) was added into the reaction and allowed to react for an additional 18 hours. At the end of the reaction period, the composition of the product was approximately 88% diester, 9% monoester and 2% stearic acid.

Due to the relatively high melting point and viscosity of the product, approximately 500 ml of toluene was added to the reaction mix and the temperature was increased to 85° C. immediately prior to filtering. The hot toluene-product mixture was then filtered under vacuum through a Whatman® qualitative filter paper, Grade 2 to remove the catalyst.

Residual toluene was removed by heating the sample to 80° C. in the round bottom flask with an egg-shaped magnetic stir bar. The flask was mounted above a magnetic stir plate and stirred while connected to dry ice trap under vacuum at about 1 mbar until product solidified due to cooling. This procedure was repeated 3 times to remove the remaining toluene. The final product was transferred to an amber bottle and sampled for purity. Product was greater than 67% PEG-150 distearate, about 28% PEG-150 monostearate and about 4% free stearic acid based on combined area percent of reactants and the products.

The method for determining the amount of 1,4-dioxane for Examples 2 and 3 was as follows:

A small amount of from about 0.02-0.04 grams of each sample was accurately weighed into a pre-cleaned thermal desorption tube with 0.5 mm OD glass bead support. The sample was mixed with the glass beads and placed in the TDS auto-sampler.

An Agilent 6890 gas chromatograph (GC) equipped with an Agilent 5975 mass selective detector (MSD) and a Gerstel thermal desorption system (TDS) configured as a sampling device was used. Each sample tube was desorbed at 60° C. for 30 minutes with a constant flow of helium gas to dynamically purge volatile components that were cold-trapped at −150° C. on the inject liner packed with small glass beads. At the end of sample desorption, the liner was rapidly heated up to 300° C. to desorb all trapped components onto the head of the GC column for separation and detection by a mass spectrometer with a scan range of 34-200 amu at 1.12 scans/second and an electron multiplier voltage at 1141 eV. The method was calibrated to 1 ppm 1,4-dioxane in methanol.

The 1,4-dioxane content in diesters of polyethyleneglycol (PEG) made using enzymatic and traditional "commercial" esterification methods was compared. Typically, these derivatizations are acid-catalyzed, which can lead to 1,4-dioxane formation via degradative cyclization. 1,4-dioxane was detected in the commercial diesters of PEG-4-dilaurate and PEG-150-distearate, but was below the limit of detection (<1 ppm) in the diesters made using an enzyme catalyst or in the PEG starting materials (see Table 1 below).

TABLE 1

| Sample | 1,4-dioxane detected |
|---|---|
| PEG-4 reactant | less than 1 ppm |
| Example 2 - PEG-4 dilaurate | less than 1 ppm |
| Commercial PEG-4 dilaurate | 314 ppm |
| PEG-150 reactant | less than 1 ppm |
| Example 3 - PEG-150 distearate | less than 1 ppm |
| Commercial PEG-150 distearate | 7 ppm |

EXAMPLE 4

Enzymatic Preparation of PEG-4 Dilaurate, Membrane Catalyst, with Catalyst Re-Use Lauric acid (29.0 g; 145 mmol; 2.0 equiv) was combined with poly (ethylene glycol) (4.5 g; 72.5 mmol; 1.0 equiv) having an average molecular weight of 204 (available from Sigma Aldrich) in a 100-mL 3 neck round bottom flask equipped with a magnetic stir bar. Immobilized *Candida antarctica* lipase B immobilized on a porous fluoropolymer support as described in US Patent Application 20120040395 was added to the flask in an amount of 2.72 grams, (8 weight %, based on total weight of starting materials). The mixture was stirred and heated to 65° C. and purged with a subsurface stream of nitrogen at a rate of 200 mL/min. After 24 hours a final sample was removed and analyzed by HPLC to determine conversion of PEG-4 to PEG-4 dilaurate was 100%.

The product mixture was removed from the flask, remaining membrane biocatalyst was acetone washed. Fresh starting materials were added in the same quantities as described above. The reaction was performed and samples were analyzed as described above. The cycle was repeated a total of three times to investigate enzyme lifetime. No appreciable degradation of activity was observed and conversion for all runs was 100%.

EXAMPLE 5

Enzymatic Preparation of PEG-4 Dioctanoate, Membrane Catalyst, with Catalyst Re-Use Octanoic acid (27.90 g; 193 mmol; 2.0 equiv) was combined with poly (ethylene glycol) 204 (6.0 g; 97 mmol; 1.0 equiv) having an average molecular weight of 204 (available from Sigma Aldrich) in a 100-mL 3 neck round bottom flask equipped with a magnetic stir bar. Immobilized *Candida antarctica* lipase B immobilized on a porous fluoropolymer support as described in US published Patent Application 2012/0040395 was added to the flask in an amount of 2.75 grams, (8 wt % based on the total weight of starting materials). The mixture was stirred and heated to 65° C. and purged with a subsurface stream of nitrogen at a rate of 200 mL/min. After 24 hours a final sample was removed and analyzed by HPLC to determine conversion of PEG-4 to PEG-4 dioctanoate was 100%.

The product mixture was removed from the flask, remaining membrane biocatalyst was acetone washed. Fresh starting materials were added in the same quantities as described above. The reaction was performed and samples were analyzed as described above. The cycle was repeated a total of three times to investigate enzyme lifetime. No appreciable degradation of activity was observed and conversion for all runs was 100%. Samples were combined for the 1,4-dioxane measurement discussed below.

EXAMPLE 6

Enzymatic Preparation of TEG Dioctanoate Using Membrane Biocatalyst

Octanoic acid (239.99 g; available from Sigma-Aldrich) was combined with triethylene glycol (average of 3 EO units, 124.97 g, available from Eastman Chemical Co.) in a 3 neck 2 liter round bottom flask equipped with a magnetic stir bar. The octanoic acid and TEG were added at a 2:1 molar ratio. Immobilized *Candida antarctica* lipase B immobilized on a porous fluoropolymer support as described in US published Patent Application 2012/0040395 was added to the flask in an amount of 29.67 g grams, (7.6 wt % based on the total weight of starting materials).

The flask was placed into a temperature controlled heating mantle and mounted above a magnetic stirrer. The mixture was stirred and heated to 65° C. and purged with a subsurface stream of nitrogen at a rate of 250 mL/min. Sampling of the reaction mixture was begun after the mixture was homogeneous. After 24 hours the reaction was stopped and filtered warm through Whatman® qualitative filter paper, Grade 2 under vacuum to remove the catalyst. The filtered product was transferred to an amber bottle and sampled for final purity. Final product was greater than 97% TEG dioctanoate based on combined area percent of reactants and the product.

EXAMPLE 7

Enzymatic Preparation of TEG Dioctanoate, Membrane Catalyst, with Catalyst Reuse Octanoic acid (19.21 g; 133 mmol; 2.0 equiv) was combined with triethylene glycol (10.0 g; 66.6 mmol; 1.0 equiv), having an average molecular weight of 150.17 (available from Eastman Chemical Company) in a 100-mL 3 neck round bottom flask equipped with a magnetic stir bar. Immobilized *Candida antarctica* lipase B immobilized on a porous fluoropolymer support as described in US Patent Application 20120040395 was added to the flask in an amount of 2.37 grams, (8 wt % based on the total weight of starting materials). The mixture was stirred and heated to 65° C. and purged with a subsurface stream of nitrogen at a rate of 200 mL/min. After 24 hours a final sample was removed and analyzed by GC to determine conversion of octanoic acid and TEG to TEG dioctanoate.

The product mixture was removed from the flask, remaining membrane biocatalyst was acetone washed. Fresh starting materials were added in the same quantities as described above. The reaction was performed and samples were analyzed as described above. The cycle was repeated a total of three times to investigate enzyme lifetime. No appreciable degradation of activity was observed. Conversion for all three runs was 97.4%, 97.9% and 98.1%, respectively.

Gas chromatographic analysis of the levels of both starting materials as well as the mono and diester products were performed on an Agilent 6890 GC equipped with a high polarity nitroterephthalic acid modified polyethylene glycol GC column and a flame ionization detector. Initial temperature was held at 40° C. for 1 minute, then a gradient from 40° C. to 300° C. over 4.3 minutes, and a final hold at 300° C. for 6 minutes, for a final run time of 11.3 minutes. Reaction progress was defined as the ratio of GC peak area percent of reactants to products.

EXAMPLE 8

Enzymatic Preparation of TEG Dilaurate, Membrane Biocatalyst, with Catalyst Reuse Lauric acid (26.70 g; 133 mmol; 2.0 equiv) was combined with triethylene glycol (10.0 g; 66.6 mmol; 1.0 equiv), having an average molecular weight of 150.17 (available from Eastman Chemical Company) in a 100-mL 3 neck round bottom flask equipped with a magnetic stir bar. Immobilized *Candida antarctica* lipase B immobilized on a porous fluoropolymer support as described in US Patent Application 20120040395 was added to the flask in an amount of 2.98 grams (8 wt % based on the total weight of starting materials). The mixture was stirred and heated to 65° C. and purged with a subsurface stream of nitrogen at a rate of 200 mL/min. After 24 hours a final sample was removed and analyzed by GC to determine conversion of lauric acid and TEG to TEG dilaurate.

The product mixture was removed from the flask, remaining membrane biocatalyst was acetone washed. Fresh starting materials were added in the same quantities as described above. The reaction was performed and samples were analyzed as described above. The cycle was repeated a total of three times to investigate enzyme lifetime. No appreciable degradation of activity was observed. Conversion for all three runs was 98.4%, 98.6% and 98.0%, respectively.

EXAMPLE 9

Enzymatic Preparation of PEG-12 Methyl Ether Monolaurate Using Novozym® 435

Lauric acid (9.0 g; 44.9 mmol; 1.0 equiv) was combined with poly (ethylene glycol) methyl ether (25.8 g; 44.9 mmol; 1.0 equiv) having an average molecular weight of 574 (available from Sigma Aldrich) in a 100-mL 3 neck round bottom flask equipped with a magnetic stir bar. Immobilized lipase Novozym®435 was added to the flask in an amount of 1.00 grams (2.9 wt % based on the total weight of starting materials). The mixture was stirred and heated to 65° C. and purged with a subsurface stream of nitrogen at a rate of 200 mL/min. After 24 hours a final sample was removed and analyzed by HPLC to determine conversion of poly(ethylene glycol) methyl ether and lauric acid to PEG-12 methyl ether dilaurate. Conversion was 100%.

EXAMPLE 10

Enzymatic Preparation of PEG-12 Methylether Palmitate Using Membrane Biocatalyst Palmitic acid methyl ester (2.00 g; 7.40 mmol) was combined with poly(ethylene glycol) (PEG-12) monomethyl ether 550 (4.41 g; 7.40 mmol; 1.0 equiv) having an average molecular weight of 596 (available from Sigma-Aldrich Chemical Company) in a 40-milliliter vial equipped with a magnetic stir bar. Immobilized *Candida antarctica* lipase B immobilized on a porous fluoropolymer support as described in US published Patent Application 2012/0040395 was added to the flask in an amount of 0.13 grams, (2 wt % based on the total weight of starting materials). The mixture was stirred and heated to 65° C. and purged with a subsurface stream of nitrogen at a rate of 100 mL/min. After 24 hours a final sample was removed and analyzed by GC to determine conversion of methyl palmitate to palmitic acid methyl ester ethoxylate. Conversion was as follows: after 3 hours, 64.8%; after 6 hours, 80.8%, after 12 hours, 92.1%; and after 23 hours, 96.4%.

The product mixture was removed from the vial and fresh starting materials were added in the same quantities as described above. The reaction was performed and samples were analyzed as before. The cycle was repeated a total of five times to investigate enzyme lifetime. No appreciable loss of enzyme activity was observed. Conversion for all five runs was 96.4%, 96.5%, 95.8%, 95.0%, and 95.2%, respectively.

Concentration of 1,4-dioxane in the product of Examples 5, 6 and 9 was determined as follows:

An equilibrium headspace (EHS) sampling technique coupled with a gas chromatograph/mass spectrometer (GC/MS) was used so as to obtain a detection limit of 1 ppm in the samples. For the lower molecular weight liquid PEG-diester samples, each sample matrix was analyzed in duplicate and the same matrix was spiked with 1 ppm of 1,4-dioxane standard in the duplicate. Therefore, four headspace sample vials per matrix are analyzed by equilibrating each vial at 60° C. for 30 min and followed by GC/MS analysis of the 1-mL headspace sample injection Five grams of each test matrix was weighed into a 22-mL HS vial. The vial was capped gas tight and analyzed in duplicate. Another 5 grams of the same sample was weighed into a 22-mL HS vial and spiked with 0.98 to 2.54 ppm (μg/g) of 1,4-dioxane calculated in the matrix in duplicate. An Agilent 6890 gas chromatograph (GC) equipped with an Agilent 5975 mass selective detector (MSD) and an Agilent 7697A headspace autosampler was used. Each sample headspace was equilibrated at 60° C. for 30 minutes in helium gas. The GC column for separation and detection by a mass spectrometer with a scan range of 34-94 amu at 1.44 scans/second and an electron multiplier voltage at 1635 eV. The 1,4-dioxane signature at m/z 88 was extracted from each chromatogram and compared to the samples spiked with 1,4-dioxane. Table 2 below details the 1,4-dioxane concentration, if any, in the starting materials and enzyme-catalyzed esters from Examples 5, 6 and 9. These materials contain less than 1 ppm (μg/g) 1,4-dioxane.

TABLE 2

| Sample | 1,4-dioxane detected |
|---|---|
| PEG-4 reactant | less than 1 ppm |
| Example 5 - PEG-4 dioctanoate | less than 1 ppm |
| TEG reactant | less than 1 ppm |
| Example 6 - TEG dioctanoate | less than 1 ppm |
| PEG-12 monomethyl ether reactant | less than 1 ppm |
| PEG-12 methylether laurate | less than 1 ppm |

EXAMPLES 11, 12 and 13

The experimental procedure of Example 2 was repeated in accordance with the method of the present invention. The reaction conditions and resulting product analysis are presented in Table 3 below.

COMPARATIVE EXAMPLE 14

The experimental procedure of Example 1 was repeated but under the reaction conditions delineated in Table 3. The product analysis is presented in Table 3 below.

COMPARATIVE EXAMPLE 15

A sample of PEG-4 dilaurate was purchased from a vendor and the composition was analyzed by HPLC. The product contained 92% diester, 7.9% monoester and no free lauric acid based on combined area percent of reactants and products. The acid number was 3.1 The 1,4-dioxane concentration was determined as described above and determined to be 314 ppm.

TABLE 3

| | Comp. Ex. 1 | Ex. 2 | Ex. 11 | Ex. 12 | Ex. 13 | Comp. Ex. 14 |
|---|---|---|---|---|---|---|
| | Reaction Conditions | | | | | |
| Catalyst load | 0.1% N435 | 5% N435 | 5% N435 | 5% N435 | 5% N435 | 0.1% N435 |
| Acid:PEG ratio | 1.9 | 2 | 2 | 2 | 2 | 2 |
| Stripping method | 10-20 mm Hg vac | 250 ml/min N₂ | 10-20 mm Hg vac | 500 ml/min N₂ | 125 ml/min N₂ | 250 ml/min N₂ |
| Rxn temp. | 60° C. | 55° C. | 55° C. | 55° C. | 55° C. | 60° C. |
| Rxn duration | 20 hrs. | 24 | 24 | 24 | 24 | 20 |
| | Product Analysis | | | | | |
| PEG-200 | 1.2 | 0 | 0 | 0 | 0 | 1.8 |
| Lauric acid | 14.3 | 0 | 0.2 | 0.3 | 0.2 | 17.7 |
| PEG-200 monolaurate | 31.3 | 0.9 | 1.7 | 2.4 | 1.5 | 32.2 |
| PEG-200 dilaurate | 53.2 | 99.1 | 98.1 | 97.2 | 98.3 | 48.2 |
| Acid No. | 88.5 | 8.2 | 16.2 | 19 | 15.2 | 96.4 |
| 1,4-dioxane | ND | Less than 1 ppm | ND | ND | ND | ND |

Having described the invention in detail, those skilled in the art will appreciate that modifications may be made to the various aspects of the invention without departing from the scope and spirit of the invention disclosed and described herein. It is, therefore, not intended that the scope of the invention be limited to the specific embodiments illustrated and described but rather it is intended that the scope of the present invention be determined by the appended claims and their equivalents. Moreover, all patents, patent applications, publications, and literature references presented herein are incorporated by reference in their entirety for any disclosure pertinent to the practice of this invention.

What is claimed is:

1. A polyoxyalkylene ester composition comprising the enzymatically catalyzed reaction product of a polyoxyalkylene alcohol or polyol reactant and an acyl donor, wherein the poloxyalkylene ester composition comprises greater than 90 weight percent of a fully acylated polyoxyalkylene ester, less than 10 weight percent of a partially acylated polyoxyalkylene ester, and 5 parts per million or less of 1,4-dioxane and an acid number of less than about 30, in each case based on the weight of the composition.

2. The ester composition of claim 1, wherein said partially acylated polyoxyalkylene ester is present in an amount of 9 weight percent or less and said fully acylated polyoxyalkylene ester is present in an amount of 91 weight percent or more.

3. The ester composition of claim 1, comprising 1,4-dioxane in an amount of 3 ppm or less.

4. The ester composition of claim 3, comprising 1,4-dioxane in an amount of 2 ppm or less.

5. The ester composition of claim 4, comprising 1,4-dioxane in an amount of 1 ppm or less.

6. A process for making a polyoxyalkylene ester composition comprising greater than 90 weight percent of a fully acylated polyoxyalkylene ester, less than 10 weight percent of a partially acylated polyoxyalkylene ester, and 5 parts per million or less of 1,4-dioxane, and having an acid number of less than 30 or less, in each case based on the weight of the composition, said process comprising:
  a) in a reaction zone, contacting a polyoxyalkylated alcohol or polyol reactant and an acyl donor reactant in the presence of an enzyme catalyst under esterification conditions to obtain said composition in said reaction zone, wherein said enzyme catalyst has a concentration of greater than about 0.1 weight % to less than 100 weight %, based on the total weight of the reactants; and
  b) recovering said polyoxyalkylene ester composition.

7. The process of claim 6 wherein said enzyme catalyst has a concentration of from about 1 weight % to about 10 weight %.

8. The process of claim 6 wherein said enzyme catalyst has a concentration of from about 3 weight % to about 8 weight %.

9. The process of any claim 6, wherein said catalyst retains greater than 40% of specific activity after heat setting.

10. The process of claim 9 wherein said catalyst retains greater than 75% of specific activity after heat setting.

11. The process of claim 6 wherein said esterification conditions includes a reaction temperature of from about 20° C. to about 120° C.

12. The process of claim 11 wherein said esterification conditions includes a reaction temperature of from about 30° C. to about 100° C.

13. The process of claim 11 wherein said esterification conditions includes a reaction temperature of from about 40° C. to about 80° C.

14. The process of claim 6, further comprising the step of removing a reaction by-product selected from the group consisting of water or a $C_1$-$C_4$ alcohol during reaction.

15. The process of claim 14 wherein said step of removing the reaction by-product includes the step of inducing a vacuum on the reaction zone sufficient to remove said by-product.

16. The process of claim 14 wherein said step of removing the reaction by-product includes the step of introducing an inert gas into the reaction zone sufficient to remove said by-product.

17. The process of claim 14 wherein said enzyme catalyst is selected from the group consisting of esterase, lipase, acylase and protease.

18. The process of claim 17 wherein the enzyme catalyst is immobilized on a substrate selected from the group consisting of solid, semi-solid, porous, organic or inorganic materials.

19. The process of claim 18 wherein said substrate is selected from the group consisting of carbon, glass, clay, silica, glyoxyl agarose, chitosan, gelatin, cellulose, cellulose esters, carboxymethylcellulose, silk, wool, cotton fibers, coconut fibers, polyethylene, polypropylene, poly(ethylene glycol), polystyrene, polyacrylamide, poly(acrylonitrile), poly(phenylendediamine), poly(ethyleneimine), polyvinyl alcohol, polyvinyl chloride, poly(ether sulfone), phenol-formalin resin, acrylic resin, fluoropolymers, anionic exchange resin, cationic exchange resin, epoxy-activated supports, amino-activated supports, octadecyl-activated supports, copolymers, blends, composites and combinations thereof.

20. The process of claim 6 wherein said recovered polyoxyalkylene ester is selected from the group consisting of: PEG-10 Laurate, PEG-10 methylether caprate, PEG-10 methylether caprylate, PEG-10 methylether caprylate/caprate, PEG-10 methylether cocoate, PEG-10 methylether isostearate, PEG-10 methylether laurate, PEG-10 methylether myristate, PEG-10 methylether oleate, PEG-10 methylether palmitate, PEG-10 methylether stearate, PEG-10 Propylene Glycol esters, PEG-10 Sorbitan Laurate, PEG-10 Stearate, PEG-10 Sunflower Glycerides, PEG-100 methylether caprate, PEG-100 methylether caprylate, PEG-100 methylether caprylate/caprate, PEG-100 methylether cocoate, PEG-100 methylether isostearate, PEG-100 methylether laurate, PEG-100 methylether myristate, PEG-100 methylether oleate, PEG-100 methylether palmitate, PEG-100 methylether stearate, PEG-100 Stearate, PEG-12 Dilaurate, PEG-12 Distearate, PEG-12 Glyceryl Dimyristate, PEG-12 Glyceryl Distearate, PEG-12 Laurate, PEG-12 Stearate, PEG-12 methylether caprate, PEG-12 methylether caprylate, PEG-12 methylether caprylate/caprate, PEG-12 methylether cocoate, PEG-12 methylether isostearate, PEG-12 methylether laurate, PEG-12 methylether myristate, PEG-12 methylether oleate, PEG-12 methylether palmitate, PEG-12 methylether stearate, PEG-120 Distearate, PEG-120 Methyl Glucose Dioleate, PEG-120 Methyl Glucose Trioleate, PEG-120 Propylene Glycol Stearate, PEG-14 Laurate, PEG-150 Dilaurate, PEG-150 Distearate, PEG-150 Laurate, PEG-150 Pentaerythrityl Tetrastearate, PEG-16 Macadamia Glycerides, PEG-16 methylether caprate, PEG-16 methylether caprylate, PEG-16 methylether caprylate/caprate, PEG-16 methylether cocoate, PEG-16 methylether isostearate, PEG-16 methylether laurate, PEG-16 methylether myristate, PEG-16 methylether oleate, PEG-16 methylether palmitate, PEG-16 methylether stearate, PEG-160 Sorbitan Triisostearate, PEG-175 Distearate, PEG-18 Glyceryl Oleate, PEG-18 Glyceryl Oleate Cocoate, PEG-18 Sorbitan Trioleate, PEG-2 Dilaurate, PEG-2 Distearate, PEG-2 Laurate, PEG-2 Sorbitan Isostearate, PEG-2 Stearate, PEG-20 Almond Glycerides, PEG-20 Dilaurate, PEG-20 Distearate, PEG-20 Glycerides, PEG-20 Laurate, PEG-20 methylether caprate, PEG-20 methylether caprylate, PEG-20 methylether caprylate/caprate, PEG-20 methylether cocoate, PEG-20 methylether isostearate, PEG-20 methylether laurate, PEG-20 methylether myristate, PEG-20 methylether oleate, PEG-20 methylether palmitate, PEG-20 methylether stearate, PEG-20 Oleate, PEG-20 Sorbitan Cocoate, PEG-20 Sorbitan Isostearate, PEG-20 Sorbitan Tetraoleate, PEG-20 Sorbitan Triisostearate, PEG-20 Stearate, PEG-200 Glyceryl Stearate, PEG-200 Hydrogenated Glycerides, PEG-200 Hydrogenated Glyceryl Palmate, PEG-200 Laurate, PEG-21 Stearate, PEG-23 Laurate, PEG-25 Hydrogenated Castor Oil, PEG-25 Propylene Glycol Stearate, PEG-3 Caprate, PEG-3 Caprylate, PEG-3 Caprylate/Caprate, PEG-3 Di(Caprylate/Caprate), PEG-3 Dicaprate, PEG-3 Dicaprylate, PEG-3 Dilaurate, PEG-3 Distearate, PEG-3 Ester of C5-C9 Acids, PEG-3 Laurate, PEG-3 Sorbitan Oleate, PEG-3 Sorbitan Stearate, PEG-30 Dipolyhydroxystearate, PEG-30 Glyceryl Cocoate, PEG-30 Glyceryl Stearate, PEG-30 Sorbitan Tetraoleate, PEG-30 Sorbitol Tetraoleate Laurate, PEG-30 Stearate, PEG-32 Dilaurate, PEG-32 Distearate, PEG-32 Laurate, PEG-32 Stearate, PEG-35 Castor Oil, PEG-4 Caprate, PEG-4 Caprylate, PEG-4 Caprylate/Caprate, PEG-4 Di(Caprylate/Caprate), PEG-4 Dicaprate, PEG-4 Dicaprylate, PEG-4 Dierucate, PEG-4 Diheptanoate, PEG-4 Dilaurate, PEG-4 Dioleate, PEG-4 Distearate, PEG-4 Laurate, PEG-4 Olivate, PEG-40 Castor Oil, PEG-40 Distearate, PEG-40 Glyceryl Cocoate, PEG-40 Hydrogenated Castor Oil, PEG-40 methylether caprate, PEG-40 methylether caprylate, PEG-40 methylether caprylate/caprate, PEG-40 methylether cocoate, PEG-40 methylether isostearate, PEG-40 methylether laurate, PEG-40 methylether myristate, PEG-40 methylether oleate, PEG-40 methylether palmitate, PEG-40 methylether stearate, PEG-40 Sorbitan Diisostearate, PEG-40 Sorbitan Hexaoleate, PEG-40 Sorbitan Laurate, PEG-40 Sorbitan Perisostearate, PEG-40 Sorbitan Peroleate, PEG-40 Sorbitan Stearate, PEG-40 Sorbitan Tetraoleate, PEG-40 Stearate, PEG-44 Sorbitan Laurate, PEG-45 Palm Kernel Glycerides, PEG-5 Ethylhexanoate, PEG-5 Glyceryl Stearate, PEG-5 Sorbitan Isostearate, PEG-50 Distearate, PEG-50 Hydrogenated Palmamide, PEG-50 Sorbitan Hexaoleate, PEG-50 Stearate, PEG-55 Propylene Glycol Oleate, PEG-6 Caprate, PEG-6 Caprylate, PEG-6 Caprylate/Caprate, PEG-6 Caprylic/Capric Glycerides, PEG-6 Cocamide, PEG-6 Di(Caprylate/Caprate), PEG-6 Dicaprate, PEG-6 Dicaprylate, PEG-6 Dilaurate, PEG-6 Distearate, PEG-6 Isostearate, PEG-6 Laurate, PEG-6 methylether caprate, PEG-6 methylether caprylate, PEG-6 methylether caprylate/caprate, PEG-6 methylether cocoate, PEG-6 methylether isostearate, PEG-6 methylether laurate, PEG-6 methylether myristate, PEG-6 methylether oleate, PEG-6 methylether palmitate, PEG-6 methylether stearate, PEG-6 Sorbitan Oleate, PEG-6 Sorbitan Stearate, PEG-6 Stearate, PEG-60 Almond Glycerides, PEG-60 Glyceryl Isostearate, PEG-60 Hydrogenated Castor Oil, PEG-60 methylether caprate, PEG-60 methylether caprylate, PEG-60 methylether caprylate/caprate, PEG-60 methylether cocoate, PEG-60 methylether isostearate, PEG-60 methylether laurate, PEG-60 methylether myristate, PEG-60 methylether oleate, PEG-60 methylether palmitate, PEG-60 methylether stearate, PEG-60 Sorbitan Stearate, PEG-60 Sorbitan Tetraoleate, PEG-60 Sorbitan Tetrastearate, PEG-60 Sorbitol Tetrastearate, PEG-7 Caprylic/Capric, Glycerides, PEG-7 Glyceryl Cocoate, PEG-7 Hydrogenated Castor Oil, PEG-7 Olivate, PEG-70 Mango Glycerides, PEG-75 Dilaurate, PEG-75 Distearate, PEG-75 Laurate, PEG-75 Propylene Glycol Stearate, PEG-75 Shea Butter Glycerides, PEG-75 Sorbitan Laurate, PEG-75 Stearate, PEG-78 Glyceryl Cocoate, PEG-8 Dicocoate, PEG-8 Dilaurate, PEG-8 Dioleate, PEG-8 Distearate, PEG-8 Isostearate, PEG-8 Laurate, PEG-8 Oleate, PEG-8 Olive Oil Ester, PEG-8 Propylene Glycol Cocoate, PEG-8 Ricinoleate, PEG-8 Stearate, PEG-80 Glyceryl Cocoate, PEG-80 Sorbitan Laurate, PEG-80 Sorbitan Palmitate, PEG-9 Distearate, PEG-9 Laurate, PEG-90 Glyceryl Isostearate, Polysorbate-20, Polysorbate-60, and Polysorbate-80.

\* \* \* \* \*